United States Patent
Razansky et al.

(10) Patent No.: US 10,292,593 B2
(45) Date of Patent: May 21, 2019

(54) IMAGING DEVICE AND METHOD FOR OPTOACOUSTIC IMAGING OF SMALL ANIMALS

(75) Inventors: Daniel Razansky, München (DE); Vasilis Ntziachristos, Gräfelfing (DE)

(73) Assignee: Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 83 days.

(21) Appl. No.: 13/386,491

(22) PCT Filed: Jul. 23, 2010

(86) PCT No.: PCT/EP2010/004542
§ 371 (c)(1),
(2), (4) Date: Apr. 5, 2012

(87) PCT Pub. No.: WO2011/012274
PCT Pub. Date: Feb. 3, 2011

(65) Prior Publication Data
US 2012/0220851 A1    Aug. 30, 2012

(30) Foreign Application Priority Data

Jul. 27, 2009 (EP) .................................. 09009683

(51) Int. Cl.
*A61B 5/00* (2006.01)
*A61B 6/00* (2006.01)
(Continued)

(52) U.S. Cl.
CPC .......... *A61B 5/0073* (2013.01); *A61B 5/0095* (2013.01); *A61B 6/508* (2013.01);
(Continued)

(58) Field of Classification Search
USPC ........................................ 600/407, 437, 476
See application file for complete search history.

(56) References Cited

U.S. PATENT DOCUMENTS

| 4,059,098 A | 11/1977 | Murdock |
| 4,180,792 A | 12/1979 | Lederman et al. |
| (Continued) | | |

FOREIGN PATENT DOCUMENTS

| EP | 0459392 | 12/1991 |
| EP | 133703 | 8/2003 |
| (Continued) | | |

OTHER PUBLICATIONS

Ku et al. "Thermoacoustic and Photoacoustic Tomography of Thick Biological Tissues Toward Breast Imaging." Technology in Cancer Research & Treatment, vol. 4, No. 5, Oct. 2005.*
(Continued)

*Primary Examiner* — Amelie R Gillman
(74) *Attorney, Agent, or Firm* — Stoel Rives LLP

(57) ABSTRACT

An imaging device configured for optoacoustic imaging of an object, including an illumination device including optical components arranged to illuminate the object, a detector device comprising an array of detector elements arranged in a tank and arranged to detect acoustic signals created in the object, and a container device including a tank arranged to accommodate the detector device, the object and a matching transmission medium, a holding device adapted to position and move the object relative to the illumination device and the detector device, wherein the optical components are arranged in the tank to illuminate the object from different directions.

14 Claims, 4 Drawing Sheets

(51) Int. Cl.
*A61B 8/13* (2006.01)
*G01N 21/17* (2006.01)
*G01N 21/39* (2006.01)

(52) U.S. Cl.
CPC ........... *A61B 8/13* (2013.01); *G01N 21/1702* (2013.01); *A61B 2503/40* (2013.01); *G01N 21/39* (2013.01); *G01N 2021/1787* (2013.01); *G01N 2201/0826* (2013.01)

(56) References Cited

U.S. PATENT DOCUMENTS

| | | |
|---|---|---|
| 4,255,971 A | 3/1981 | Rosenewaig |
| 4,343,993 A | 8/1982 | Bining et al. |
| 4,385,634 A | 5/1983 | Bowen |
| 4,646,756 A | 3/1987 | Watmough et al. |
| 4,770,183 A | 8/1988 | Groman et al. |
| 4,986,275 A | 1/1991 | Ishida et al. |
| 5,411,730 A | 5/1995 | Kirpotin et al. |
| 5,840,023 A | 11/1998 | Oraevsky et al. |
| 5,924,991 A | 7/1999 | Hossack et al. |
| 6,070,093 A | 5/2000 | Oosta et al. |
| 6,102,857 A | 8/2000 | Kruger |
| 6,173,604 B1 | 1/2001 | Xiang |
| 6,208,749 B1 | 3/2001 | Gutkowicz-Krusin et al. |
| 6,216,025 B1 | 4/2001 | Kruger |
| 6,263,221 B1 | 7/2001 | Chance et al. |
| 6,424,410 B1 | 7/2002 | Pelosi |
| 6,428,171 B1 | 8/2002 | Aoki et al. |
| 6,445,453 B1 | 9/2002 | Hill |
| 6,477,398 B1 | 11/2002 | Mills |
| 6,498,492 B1 | 12/2002 | Rezvani |
| 6,526,298 B1 | 2/2003 | Khalil et al. |
| 6,567,688 B1 | 5/2003 | Wang |
| 6,615,063 B1 | 9/2003 | Ntziachristos et al. |
| 6,641,798 B2 | 11/2003 | Achilefu et al. |
| 6,662,040 B1 | 12/2003 | Henrichs et al. |
| 6,700,459 B2 | 3/2004 | Raihn et al. |
| 6,760,609 B2 | 7/2004 | Jacques |
| 6,768,265 B1 | 7/2004 | Ives et al. |
| 7,005,653 B1 | 2/2006 | O'Connell et al. |
| 7,298,869 B1 | 11/2007 | Abernathy |
| 7,510,555 B2 | 3/2009 | Kanzius |
| 7,515,948 B1 | 4/2009 | Balberg et al. |
| 7,894,885 B2 | 2/2011 | Bartel et al. |
| 2002/0026106 A1 | 2/2002 | Khalil et al. |
| 2002/0048077 A1* | 4/2002 | Fukumoto ............... 359/330 |
| 2002/0073717 A1 | 6/2002 | Dean |
| 2002/0163735 A1 | 11/2002 | Detlef et al. |
| 2002/0193678 A1 | 12/2002 | Kruger |
| 2003/0018262 A1 | 1/2003 | Manor et al. |
| 2003/0023152 A1 | 1/2003 | Abbink et al. |
| 2003/0135110 A1 | 7/2003 | Leussier |
| 2004/0054268 A1 | 3/2004 | Esenaliev et al. |
| 2004/0059265 A1 | 3/2004 | Candy et al. |
| 2004/0067000 A1* | 4/2004 | Bates et al. .............. 385/7 |
| 2004/0127783 A1 | 7/2004 | Kruger |
| 2004/0176805 A1 | 9/2004 | Whelan |
| 2004/0181153 A1 | 9/2004 | Hall |
| 2004/0210126 A1* | 10/2004 | Hajaj ............ A61B 6/032 600/407 |
| 2004/0232321 A1 | 11/2004 | Mervyn et al. |
| 2004/0254457 A1 | 12/2004 | vander Weide |
| 2005/0150309 A1* | 7/2005 | Beard ............ 73/861.18 |
| 2005/0154308 A1 | 7/2005 | Quistgaard et al. |
| 2005/0175540 A1 | 8/2005 | Oraevsky et al. |
| 2005/0234319 A1 | 10/2005 | Mandelis et al. |
| 2006/0058685 A1 | 3/2006 | Fomitchov et al. |
| 2006/0064001 A1 | 3/2006 | Barbour |
| 2006/0084861 A1 | 4/2006 | Blank et al. |
| 2006/0184042 A1 | 8/2006 | Wang et al. |
| 2006/0256339 A1 | 11/2006 | Lowney et al. |
| 2006/0264717 A1 | 11/2006 | Pesach et al. |
| 2007/0015992 A1 | 1/2007 | Filkins et al. |
| 2007/0152144 A1 | 7/2007 | Quake |
| 2007/0197886 A1 | 8/2007 | Naganuma et al. |
| 2007/0238954 A1* | 10/2007 | White et al. ............. 600/407 |
| 2007/0238958 A1 | 10/2007 | Oraevsky et al. |
| 2007/0274580 A1 | 11/2007 | Ntziachristos et al. |
| 2008/0071172 A1 | 3/2008 | Bruck et al. |
| 2008/0118934 A1 | 5/2008 | Gerdes |
| 2008/0123083 A1 | 5/2008 | Wang et al. |
| 2008/0173093 A1* | 7/2008 | Wang et al. ............. 73/602 |
| 2008/0221647 A1 | 9/2008 | Chamberland et al. |
| 2008/0228073 A1 | 9/2008 | Silverman et al. |
| 2009/0024038 A1 | 1/2009 | Arnold |
| 2009/0038375 A1 | 2/2009 | Breuer et al. |
| 2009/0054763 A1 | 2/2009 | Wang et al. |
| 2009/0058746 A1 | 3/2009 | Delgado |
| 2009/0081122 A1 | 3/2009 | Rufenacht et al. |
| 2009/0192358 A1 | 7/2009 | Jaffer et al. |
| 2009/0324048 A1* | 12/2009 | Leevy ............ A61B 5/0059 382/132 |
| 2010/0022866 A1* | 1/2010 | Feke et al. ............. 600/407 |
| 2010/0078576 A1 | 4/2010 | Ntziachristos et al. |
| 2010/0249570 A1 | 9/2010 | Carson et al. |
| 2011/0001975 A1 | 1/2011 | Razansky et al. |
| 2011/0040176 A1 | 2/2011 | Razansky et al. |
| 2011/0201914 A1 | 8/2011 | Wang et al. |
| 2011/0208057 A1 | 8/2011 | Oikawa |
| 2011/0231160 A1 | 9/2011 | Suzki |
| 2011/0282192 A1 | 11/2011 | Axelrod et al. |
| 2011/0301453 A1 | 12/2011 | Ntziachristos et al. |
| 2011/0306865 A1 | 12/2011 | Thornton et al. |
| 2012/0029829 A1 | 2/2012 | Li et al. |
| 2012/0150012 A1 | 6/2012 | Fujimoto et al. |
| 2012/0238873 A1 | 9/2012 | Lacoste et al. |
| 2013/0041267 A1 | 2/2013 | Ntziachristos et al. |
| 2013/0312526 A1 | 11/2013 | Oishi |
| 2014/0114187 A1 | 4/2014 | Rozenthal et al. |
| 2014/0198606 A1 | 7/2014 | Mitchell et al. |
| 2014/0336505 A1 | 11/2014 | Ripoll Lorenzo et al. |
| 2014/0363066 A1 | 12/2014 | Ntziachristos et al. |

FOREIGN PATENT DOCUMENTS

| | | |
|---|---|---|
| EP | 1561424 | 8/2005 |
| EP | 2695893 | 8/2012 |
| JP | 09219563 | 8/1997 |
| JP | 2004351023 | 12/2004 |
| JP | 2007/307007 | 11/2007 |
| JP | 2010125260 | 6/2010 |
| JP | 2012170762 | 9/2012 |
| WO | WO2004/068405 | 8/2004 |
| WO | WO2006/061829 | 6/2006 |
| WO | WO2006/063246 | 6/2006 |
| WO | WO2007/084771 | 7/2007 |
| WO | 2007/100937 A2 | 9/2007 |
| WO | 2007/111669 A2 | 10/2007 |
| WO | WO2008/018082 | 2/2008 |
| WO | WO2008/101019 | 8/2008 |
| WO | WO2009/055095 | 4/2009 |
| WO | 2010/009747 A1 | 1/2010 |
| WO | 2011/000389 A1 | 1/2011 |
| WO | WO2011/072198 | 6/2011 |
| WO | WO2011/137385 | 11/2011 |
| WO | WO2012/108170 | 8/2012 |
| WO | WO2012/108172 | 8/2012 |
| WO | WO2012/137855 | 10/2012 |
| WO | WO2012/150721 | 11/2012 |
| WO | WO2013/185784 | 12/2012 |
| WO | WO2013/167147 | 11/2013 |
| WO | WO2014/066150 | 5/2014 |

OTHER PUBLICATIONS

Capps, "Near Field or Far Field?", EDN Network, www.ednmag.con Aug. 16, 2001, p. 95-102.
Office Action dated Jun. 3, 2013 for U.S. Appl. No. 12/867,265.
Office Action dated Jun. 18, 2013 for U.S. Appl. No. 13/055,552.
Razansky, D. et al., "Hybrid Photoacoustic Fluorescence Molecular Tomography Using Finite-Element-Based Inversion," *Med. Phys.*, Nov. 2007, vol. 34, No. 11, pp. 4293-4301.

(56) References Cited

OTHER PUBLICATIONS

Larin, K.V. et al., "Monitoring of Tissue Coagulation during Thermotherapy Esing Optoacoustic Technique," *Journal of Physics D: Applied Physics*, 2005, vol. 38, pp. 2645-2653.
"American National Standard for Safe Use of Lasers," *Laser Institute of America*, ANSIZ136-2007 (revision of ANSI Z136.1-2000), cover, contents and pp. 1-249.
U.S. Appl. No. 12/867,265, filed Sep. 20, 2010, Razansky et al.
U.S. Appl. No. 13/381,207, filed Jan. 27, 2012, Razansky et al.
U.S. Appl. No. 13/055,552, filed Feb. 23, 2011, Razansky et al.
Ash et al., 'Super-Resolution Aperture Scanning Microscope', Nature, vol. 237, Jun. 30, 1972, pp. 510-512.
Laufer et al., 'Quantitative Spatially Resolved Measurement of Tissue Chromophore Concentrations Using Photoacoustic Spectroscopy: Application to the Measurement of Blood Oxygenation and Haemoglobin Concentration', Phys Med Biol, 2007, vol. 52, pp. 141-168.
Chen et al., 'Atomic Decomposition by Basis Pursuit', SIAM Review, 2001, vol. 43 No. 1, pp. 129-159.
Jetzfellner et al., 'Preformance of Interactive Optoacoustic Tomography with Experimental Data', Applied Physics Letters, 2009, vol. 95, pp. 013703.1-013703.3.
Cox et al., 'Gradient-Based Quantitative Photoacoustic Image for Molecular Imaging', Proc of SPIE, 2007, vol. 6437, pp. 643IT.1-643IT.10.
Cox et al., 'Two-Dimensional Quantitative Photoacoustic Image Reconstruction of Absorption Distributions in Scattering Medica by Use of a Simple Iterative Method', Applied Optics, Mar. 10, 2006, vol. 45 No. 8, pp. 1866-1873.
Paltauf et al., 'Iterative Reconstruction Algorithm for Optoacoustic Imaging', J Acoust Soc Am, Oct. 2002,vol. 112 No. 4, pp. 1536-1544.
Jiang et al., 'Spatially Varying Optical and Acoustic Property Reconstruction Using Finite-Element-Based Photoacoustic tomography', J Opt Soc Am, Apr. 2006, Vo. 23 No. 4, pp. 878-888.
Intes et al. 'Projection Access Order in Algebraic Reconstruction Technique for Diffuse Optical Tomography', Phys Med Biol, 2002, vol. 47, pp. N1-N10.
Office Action dated Dec. 7, 2012 for U.S. Appl. No. 13/055,552.
Vinegoni et al., 'In vivo Imaging of *Drosophila metanogaster* Pupae with Mesoscopic Fluorescence Tomography', Nature Methods, Jan. 2008, vol. 5 No. 1, pp. 45-47 and Supplementary Notes.
Zacharakis et al., 'volumetric Tomography of Fluorescent Proteins Through Small Animals In Vivo', PNAS, Dec. 20, 2005, vol. 102 No. 51, pp. 18252-18257.
Yuan et al., 'Quantitative Photoacoustic Tomography: Recovery of Optical Absorption coefficient Maps of Haterogeneous Media', Applied Physics Letters 88:231101, 2006.
Razansky et al., 'Multispectral Photoacoustic Imaging of Fluorochromes in Small Animals', Optics Letters, vol. 23, No. 19, pp. 2891-2893, Oct. 1, 2007.
Rosenthal et al., 'Quantitative Optoacoustic Signal Extraction Using Sparse Signal Repesentation', IEEE Transactions on Medical Imaging, vol. 28, No. 12, pp. 1997-2006, 2009.
Xu et al., 'Exact Frequency-Domain Reconstruction for Thermoacoustic Tomography—I: Planar Geometry', IEEE Transactions on Medical Imaging, vol. 21, No. 7, pp. 823-828, 2002.
Oraevsky et al., 'Direct Measurement of Laser Fluence Distribution and Optoacoustic Imaging in Heterogeneous Tissues', Proc SPIE 2323, Laser Interactions with Hard and Soft Tissue 11, 37, 1995.
Karabutov et al., 'Optoacoustic Measurement of Optical Properties of Turbid Media', Proc. SPIE vol. 4749, pp. 288-298, 2002.
Razansky et al., 'Multispectral Opto-Acoustic Tomography of Deep-Seated Fluorescent Proteins in Vivo', Nature Photonics, 3, 412-417, 2009.
Schulz et al., 'Experimental Fluorescence Tomography of Tissues with Noncontact Measurements', IEEE Transactions on Medical Imaging, Vo. 23, No. 4, oo 492-500, 2004.
Ripoll et al., 'Free-Space Propagation of Diffuse Light: Theory and Experiments', Phys. Rev, Lett., vol. 91, No. 10, pp. 103901-1-103901-6, 2003.
Zibulevsky et al., 'Blind Source Separation by Sparse Decomposition', ICA, Principle and Practice, Chapter 7, Cambridge, 2001.
U.S. Appl. No. 14/102,328, filed Dec. 10, 2013, Kacprowicz.
U.S. Appl. No. 14/102,250, filed Dec. 10, 2013, Razansky et al.
Office Action dated Jan. 14, 2014 for U.S. Appl. No. 13/055,552.
Office Action dated Jan. 29, 2014 for U.S. Appl. No. 12/867,265.
Sugiyama et al., 'Character Pattern Recognition Utilizing Independent Component', Proceedings of the 44th Conference of the Institute of Systems, Control and Informaiton Engineers (ISCIE), p. 457-458, nglish abstract, 2000.
Taruttis et al., 'Motion Clustering for Deblurring Multispectral Optoaxoustic Tomography Images of the Mouse Heart', Journal of Biopmedical Optics, vol. 17, No. 1, pp. 16009-1 to 16009-4, Jan. 2012.
Taruttis et al., 'Imaging the Small Animal Cardiovascular System in Real-Time with Multispectral Optoacoustic Tomography', Proc of SPIE, vol. 7899, pp. 789913-1 to 789913-8, 2011.
Buehler et al., 'Video Rate Optoacoustic Tomography of Mouse Kidney Perfusion', Optics Letters, vol. 35, No. 14, pp. 2475-2477, Jul. 15, 2010.
Glatz et al., 'Blind Source Unmixing in Multi-Spectral Optoacoustic Tomography', Optics Express, vol. 19, No. 4, pp. 3175-3184, Feb. 14, 2011.
Morscher et al., 'Spectral Unmixing Using Component Analysis in Multispectral Optoacoustic Tomography', Proc SPIE, vol. 8089, 2011.
Morscher et al., 'Blind Spectral Unmixing to Identify Molecular Signatures of Absorbers in Multispectral Optoacoustic Tomography', Proc SPIE, Photons Plus Ultrasound: Imaging and Sensing, vol. 7899, 2011.
U.S. Appl. No. 13/399,272, filed Nov. 6, 2014, Kellnberger et al.
Office Action dated Oct. 6, 2014 for U.S. Appl. No. 13/381,207.
Office Action dated Oct. 29, 2014 for U.S. Appl. No. 13/055,552.
Office Action dated Dec. 26, 2014 for U.S. Appl. No. 12/867,265.
Xu et al., 'Universal Back-Projection Algorithm for Photoacoustic Computed Tomography', The American Physical Society,Physical Review, vol. E71, No. 1, pp. 016706, 2005.
Skolnik, Radar Handbook, McGraw Hill, Chapter 8, 2008.
Ye, 'PSTD Method of Thermoacoustic Tomography (TAT) and Related Experimental Investigation', Dissertation, 2009.
Telenkov et al., 'Frequency-Domain Photothermoacoustics: Alternative Imaging Modality of Biological Tissues', Journal of Applied Physics, vol. 105, p. 102029, 2009.
Fan et al., 'Development of a Laser Photothermoacoustic Frequency-Swept System for Subsurface Imaging: Theory and Experiment', J. Acoust. Soc. Am., 116(6), 2004.
Skolnik, Introduction to Radar Systems, Chapter 6.5, McGraw Hill, 2001.
Skolnik, Introduction to Radar Systems, Chapter 11.5, McGraw Hill, 1981.
Rosenthal et al., 'Fast Semi-Analytical Model-Based Acoustic Inversion for Quantitative Optoacoustic Tomography', IEEE Transactions on Medical Imaging, vol. 29, No. 6, Jun. 2010.
Baddour, 'Theory and Analysis of Frequency-Domain Photoacoustic Tomography', J. Acoust. Soc. Am., 123(5), pp. 2577-2590, 2008.
Paltauf et al., 'Three-Dimensional Photoacoustic Tomography Using Acoustic Line Detectors', Soc. Opt. Eng., vol. 6437,pp. 1-10, 2007.
Maslov et al., 'Photoacoustic Imaging of Biological Tissue with Intensity-Modulated Continuous-Wave Laser', Journal of Biomedical Optics, vol. 13, No. 2, pp. 024006, 2008.
Kak et al., 'Principles of Computerized Tomographic Imaging', IEEE Press, Chapters 3 and 6, 1988.
International Preliminary Report dated Dec. 24, 2014 for PCT/EP2012/002466.
Wang, 'Multiscale Photoacoustic Microscopy and Computed Tomography', Nature Photonics, Review Article, 2009.
Zhang et al., 'Collecting Back-Reflected Photons in Photoacoustic Microscopy', Optics Express, vol. 18, No. 2, Jan. 18, 2010.
Wang et al., 'Photoacoustic Tomography: In Vivo Imaging from Organelles to Organs', Science, 335(6075), Mar. 23, 2012.

(56) References Cited

OTHER PUBLICATIONS

Yao et al.; 'Photoacoustic Tomography: Fundamentals, Advances and Prospects', contrast Media Mol Imaging 6(5), 2011.
Li et al., 'Fast-Scanning Reflection-Mode Integrated Photoacoustic and Optical-coherence Microscopy', Proc. of SPIE, vol. 7564, 2010.
Ntziachristos, 'Going Deeper than Microscopy: The Optical Imaging Frontier in Biology', Nature Methods, vol. 7, No. 8, 2010.
Aguirre et al., 'A curved Array Photoacoustic Tomography System for Small Animal Imaging', Proc, SPIE 6437:OV1-OV10, 2007.
Allen et al., 'Dual Wavelength Laser Diode Excitation Source for 2D Photoacoustic Imaging', Proc. SPIE 6437: U1-U9, 2007.
Erpelding et al., 'Three-Dimensional Photoacoustic Imaging with a Clinical Two-Dimensional Matrix Ultrasound Transducer', Photons Plus Ultrasound: Imaging and Sensing, Proc of SPIE, vol. 7899, 2011.
Office Action dated May 7, 2015 for U.S. Appl. No. 13/381,207.
Office Action dated Jul. 14, 2015 for U.S. Appl. No. 14/102,250.
Office Action dated Jul. 14, 2015 for U.S. Appl. No. 14/102,328.
Office Action dated Jul. 30, 2015 for U.S. Appl. No. 13/055,552.
Office Action dated Oct. 2, 2015 for U.S. Appl. No. 12/867,265.
Philips. White Pate for iU22 with X7-2 Probe, 2010, 1 pg, internet. https://web.archive.org/web/20100908015304/http://healthcare.philips.com/main/products/ultrasound/transducers/7x_2.wpd.
Pratt, 'Image Sampling and Reconstruction,' Digital Image Processing: PIKS Scientific Inside by William K. Pratt, pub. Wiley-Interscience; 4 Edition (Feb. 9, 2007); ISBN: 0471767778; Chapter 4.
Song, 'High-Speed Photoacoustic Microscopy in Vivo', Ph.D. Thesis, School of Eng. & Appl. Sci., Washington University, Saint Louis, 133 pgs, 2010.
Viator et al., 'Clinical Testing of a Photoacoustic Probe for Port-Wine Stain Depth Determination', Lasers Surg. Med. 30:141-148, 2002.
Yin et al., 'Tomographic Imaging of Absolute Optical Absorption Coefficient in Turbid Media Using combined Photoacoustic and Diffusing Light Measurements', Optics Letters, vol. 32 No. 17, pp. 2556-2558, 2007.
U.S. Appl. No. 14/102,328, Non-Final Office Action, dated Aug. 26, 2016, 29 pages.
Final Office Action dated Jan. 21, 2016 for U.S. Appl. No. 14/102,328.
Final Office Action dated Feb. 19, 2016 for U.S. Appl. No. 14/102,250.
Non-Final Office Action dated Dec. 3, 2015 for U.S. Appl. No. 14/141,773.
Office Action dated Mar. 11, 2016 for U.S. Appl. No. 13/055,552.
Xu, et al., "Time-Domain Reconstruction for Thermoacoustic Tomography in a Spherical Geometry", IEEE Transactions on Medical Imaging vol. 21, No. 7, Jul. 2002, 814-822.
Office Action dated Jun. 9, 2016 for U.S. Appl. No. 14/141,773.
Office Action dated Mar. 20, 2017 for U.S. Appl. No. 14/102,328.
U.S. Appl. No. 14/102,250, et al., Non-Final Office Action, dated Mar. 13, 2017, 42 pages.
Andreev,V.G. et al.,Inverse radon transformation for optoacoustic imaging, Biomedical Optoacoustics II, 4618 ,2002 ,pp. 137-145.
U.S. Appl. No. 12/867,265, Final Office Action, dated Dec. 16, 2016, 44 pages.
U.S. Appl. No. 14/141,773, Notice of Allowance, dated Oct. 25, 2016, 21 pages.
U.S. Appl. No. 13/055,552, Notice of Allowance, dated Nov. 18, 2016 13 pages.

* cited by examiner

IMAGING DEVICE AND METHOD FOR OPTOACOUSTIC IMAGING OF SMALL ANIMALS

RELATED APPLICATIONS

This is a § 371 of International Application No. PCT/EP2010/004542, with an international filing date of Jul. 23, 2010 (WO 2011/012274 A1, published Feb. 3, 2011), which is based on European Patent Application No. 09009683.5, filed Jul. 27, 2009, the subject matter of which is incorporated by reference.

TECHNICAL FIELD

This disclosure relates to imaging devices configured for optoacoustic imaging of an object and imaging methods for optoacoustic imaging of an object. In particular, the disclosure relates to devices and methods for quantitative three-dimensional sensing and imaging of target tissue biomarkers, in particular in clinical, small animal and small organism imaging applications using multiple-wavelength illumination.

BACKGROUND

Multi-spectral optoacoustic tomography (MSOT) is a method capable of resolving chromophoric agents with molecular specificity through several millimeters to centimeters of tissue. The technique is based on the optoacoustic phenomenon, i.e., generation of acoustic waves due to thermoelastic expansion caused by absorption of ultra-short optical pulses. Optoacoustic interrogation of living tissues is recently drawing vast attention due to its ability of preserving scattering-free spatial resolution deep in highly scattering tissues while providing rich contrast characteristic of optical spectrum. Over the last decade, optoacoustics has been considered for tissue imaging, mainly for resolving vascular contrast and the corresponding physiological changes, in particular oxy- and deoxy-hemoglobin, superficial vascular anatomy, brain lesion and functional cerebral hemodynamic changes, blood volume and oxygen consumption changes and the associated dynamic and functional neuronal activities.

The main difficulty arising from 3D optoacoustic imaging is the long acquisition times associated with recording signals from multiple spatial projections. In tomographic applications, to attain the best quality quantified reconstructions, the optoacoustic responses have to be collected from as many locations as possible around the imaged object or region of interest.

The generated optoacoustic waves need an acoustically-matched medium to effectively propagate and reach the detector's surface. As an example, arrangement of the object to be imaged and a detector element in a container with water have been proposed (see D. Razansky and V. Ntziachristos, "Med. Phys.," Vol. 34, 2007, pp. 4293-4301). This technique may have the following disadvantages.

Placement of the detector element at different locations for collecting optoacoustic responses requires a translation stage, which is arranged in the container. Operating a translation stage in water may result in malfunctions and non-reproducible positioning. Furthermore, the container technique has been demonstrated with synthetic phantoms. In case of biological imaging, the container technique would require placement of the imaged object or region of interest into the water or other liquid media for coupling. This however imposes severe practical limitations. If, for instance, a living animal being imaged resides in water, variety of hygienic, epidemiological and general handling issues readily arise. Moreover, many areas of the body become inaccessible for imaging unless the animal is submerged entirely into the liquid, which requires specialized breathing accessories and further complicates the overall imaging configuration and abilities for fast and reliable data acquisition.

The generated optoacoustic responses are generally weak and the SNR is low, problems that are usually solved by multiple signal averaging, which only further complicates matters and makes imaging challenging for most applications, especially those dealing with living subjects. For instance, one could obtain a rough estimate on the order of magnitude of a typical optoacoustic disturbance by considering a simplified one-dimensional case of a short pulsed beam impinging upon absorbing half space. Under heat and temporal stress confinement conditions, pressure-rise distribution P(r) can be expressed as $$P(r) = \frac{\beta C_s^2}{C_P} \mu_a(r)\phi(r) = \Gamma \mu_a(r)\phi(r),$$

where the typical parameters for biological tissue are $\beta = 3 \cdot 10^{-4}$ (° C.$^{-1}$) for the thermal expansion coefficient; $C_s = 15 \cdot 10^{-4}$ (cm s$^{-1}$) for the speed of sound; $C_p = 4.186$ (J g$^{-1}$° C.$^{-1}$) for the specific heat capacity at constant pressure; and $\mu_a = 0.3$ cm$^{-1}$ for the optical absorption coefficient (see K. V. Larin et al. in "Journal of Physics D-Applied Physics," vol. 38(15), 2005, p. 2645-2653). In a typical imaging scenario, illumination of tissue with maximal permissible fluence of $\phi = 20$ mJ/cm$^2$ will only result in optoacoustic disturbances with less than 1 kPa magnitude on the tissue surface light is incident upon, which will translate into an order of magnitude lower detectable pressure variations on the detector's surface. If deep tissue imaging is of interest, the pressure variations will be further affected by light attenuation and acoustic dispersions, which will bring the signals down by another order of magnitude and more so that only few Pascals are available for detection. Finally, when considering multispectral optoacoustic tomography (MSOT) data acquisition, in which tomographic data is recorded at several different wavelengths, 3D image acquisition times readily become unrealistic.

Alternatively, spreading multiple small-area (point) detectors around the object along with signal averaging may only moderately improve the SNR and acquisition times. This is due to the fact that the noise floor is inversely proportional to square root of the number of signal averages. From the practical imaging perspective and SNR considerations it is therefore always desirable to increase detection sensitivity rather than reduce the thermal noise by using multiple measurements/averages.

It could therefore be helpful is to provide improved imaging devices for optoacoustic imaging of an object avoiding disadvantages and limitations of conventional techniques. In particular, it could be helpful for the improved imaging device to be capable of high performing and quantitative optoacoustic imaging. Furthermore, it could be helpful to provide improved imaging methods for optoacoustic imaging of an object. Of particular interest is the development of fast-acquisition imaging approaches for whole body imaging of model organisms and disease biomarkers in vivo that will enable studying fast-varying bio-

SUMMARY

We provide an imaging device configured for optoacoustic imaging of an object, including an illumination device including optical components arranged to illuminate the object, a detector device including an array of detector elements arranged in a tank and arranged to detect acoustic signals created in the object, and a container device including a tank arranged to accommodate the detector device, the object and a matching transmission medium, a holding device adapted to position and move the object relative to the illumination device and the detector device, wherein the optical components are arranged in the tank to illuminate the object from different directions.

We also provide an imaging method of optoacoustic imaging of an object, including positioning the object with a holding device in a tank of a container device, in which tank a matching transmission medium and a detector device are included, illuminating the object via optical components of an illumination device, detecting acoustic signals created in the object with the detector device, wherein the object is moved with the holding device relative to the illumination device and the detector device during the detecting of the acoustic signals, and reconstructing an image of the object by analyzing the acoustic signals, wherein the optical components are arranged in the tank to illuminate the object from different directions, and the acoustic signals are detected with an array of detector elements arranged in the tank.

DETAILED DESCRIPTION

Figure 1:
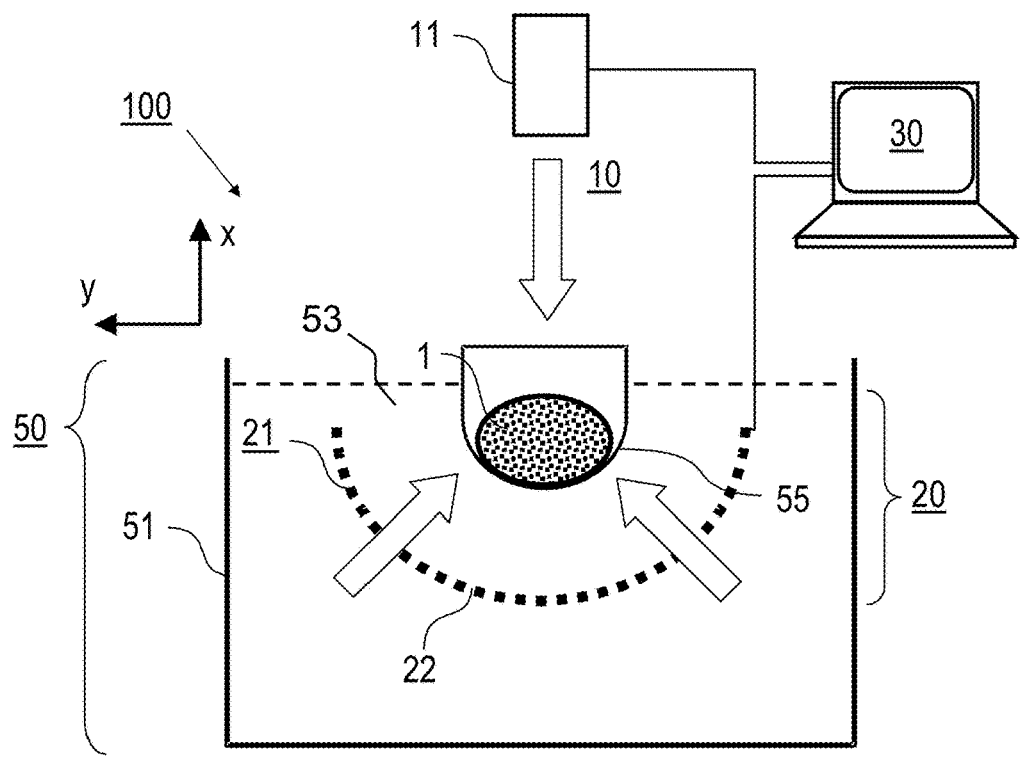
FIGS. 1 and 2 are schematic illustrations of a preferred imaging device.

An imaging device may be configured for optoacoustic imaging of an object comprising an illumination device including optical components arranged for a pulsed illumination of the object, a detector device arranged for a detection of acoustic signals created in the object, and a container device arranged for accommodating the detector device, the object and a matching transmission medium (in particular matching fluid). The container device accommodates a holding device capable of positioning the object in the container. The imaging device is configured such that the holding device with the object and the illumination and detector devices are movable relative to each other.

An imaging method of optoacoustic imaging an object may comprise the steps of positioning the object with a holding device in a container device, which includes a matching transmission medium and a detector device, illuminating the object via optical components of an illumination device, detecting acoustic signals created in the object in response to the illumination with the detector device, and reconstructing a tomographic image of the object by analyzing the acoustic signals. During the detection of the acoustic signals, the holding device with the object and the illumination and detector devices are moved relative to each other.

At least some of the optical components of the illumination device are arranged in the container device. Furthermore, the optical components of the illumination device are arranged such that the object can be illuminated from different directions. The optical components comprise any element adapted to deflect and/or focus a light beam directed to the object. As an advantage, a patterned illumination of a predetermined region of interest, in particular a predetermined detection plane in the object can be obtained by distributing the optical components on different sides of the object. The optical components can be positioned in immediate neighborhood of the holding device accommodating the object. Preferably, the illumination pattern is a line illumination perpendicular to the object axis. The line illumination can be projected from multiple angles surrounding the object and their intensity can be varying across the line to create a homogenous or close to homogenous light delivery around the object's surface. Contrary to conventional techniques, distortions by a container wall or other parts of the experimental setup can be avoided and the illumination intensity can be essentially increased by exclusively concentrating the illumination power or energy on the region of interest. As the acoustic signals are detected, the object is moved with the holding device relative to the optical components of the illumination device or, alternatively, the optical system scans the pattern on the object. With this movement (scanning movement), the region of interest, in particular the detection plane is shifted through the object. Generally, the movement can comprise a rotation and/or a translation.

Furthermore, the detector device comprises an array of detector elements which is arranged in the container device. While a single detector can be used, which is time-shared at multiple position, it is an advantage to employ a detector array so that optoacoustic responses are collected at different locations simultaneously. The array of detector elements comprises any device which includes multiple detector elements at predetermined fixed positions. Preferably, the detector elements are distributed along a predetermined straight or curved line (or plane or curved surface) in space, in correspondence to the line (or surface) illumination pattern established so that the detectors detect from the volume illuminated. The detector elements can be arranged side by side adjacent to each other and/or with mutual spacings. During the detection of the acoustic signals, the object may be moved with the holding device relative to the array of detector elements (scanning movement) or the detection, the illumination or both may be moved relative to the object.

The proposed solution utilizes parallel detection configuration using multiple large-area focused ultrasonic detection elements for fast data acquisition. Both illumination and detection topologies are optimized for fast data acquisition and real-time image reconstruction. The optoacoustic data is sequentially collected at multiple excitation wavelengths to construct images of the target representing anatomical and functional information as well as distribution of intrinsic or extrinsically administered biomarkers and contrast agents. The detectors can be effectively focused along a line (cylindrically focused perpendicular to the objects axis in analogy to the illumination pattern). However other patterns can be foreseen implemented, for example, spherically-focused elements or arrangements or unfocused elements for collection of three-dimensional data.

Preferably, our devices and methods image tissue of small animals, tissue of mesoscopic size, i.e., tissue having a typical dimension in the range of 100 µm to 10 cm or more, e.g., 100 µm to 5 cm, in particular from 1 mm to 3 cm, or tissue or a tissue component of a human body (or an animal body having a size comparable with a human body).

Preferably, the images of the object reconstructed during the scanning movement comprise 2D images collected and reconstructed in real time. Imaging in real time means that a 2D single or multi wavelength image is collected within a time below 2 s, e.g., below 1 s, in particular below 500 ms. A 3D image can be constructed based on a series of 2D images of the object along the detection planes scanned during the scanning movement. The series of 2D images is preferably collected by stepwise adjusting the object relative to a detection plane of the detector device, illuminating the object with pulsed illumination light and detecting of the acoustic signals with the adjusted object position, wherein the illuminating and detecting steps are repeated at least twice, e.g., 3, 4, 5, or more times with different wavelengths of the illumination light. For constructing the 3D image, a series of at least 5 slices, e.g., 20 slices, preferably 100 slices, like 200 slices or even more is collected.

Preferably, the detector device comprises an array of focused detector elements which are focused into the predetermined region of interest, in particular the predetermined detection plane in the object. Advantageously, this results in an increased signal-to-noise-ratio of the signal collection. Focused detector elements have a sensitivity profile with a main sensitivity direction (focusing direction). Preferably, the detector elements comprise at least one of piezoelectric film detector elements, and film detector elements adapted for interferometric signal recording.

Further preferably, the detector elements are arranged along an arc at least partially surrounding the object. The detector device is configured such that the arc-shaped (e.g., semicircle-shaped) array of detector elements at least partially surrounds the path of movement of the object and the detector array relative to each other. The detector elements are spanned along a detection plane, through which the object is scanned for 3D imaging.

Preferably, the imaging device provides a semi-cylindrical (180 degrees) detection geometry. The arc of detector elements spans 180°. An advantage of this geometry is that it allows the object to be "immersed" in the matching medium and allow a better viewing angle (projections) by a (cylindrical) detection geometry.

As a further advantage, there are no particular limitations with regard to the type of optical components used, which preferably may comprise optical mirrors or optical fibers located in the container. Optical fibers are particularly preferred as optical fibers are capable of guiding the illumination light pulses with minimum losses towards the object. The optical fibers may comprise a fiber bundle having multiple arms, e.g., at least three arms, preferably at least 5 arms, e.g., 10 arms or more. Preferably, the optical fibers are arranged at equally spaced angles along an azimuthal line surrounding the object. Further preferably, the optical components, preferably the optical fibers, are arranged for illuminating the object with a ring type pattern.

The holding device may comprise a rod or plate shaped holding element arranged for carrying the object. The object can be directly connected with the rod or plate shaped holding element. In this case, the object is directly immersed in the matching transmission medium in the container. According to an alternative, the holding device preferably comprises a membrane arranged for accommodating the object. The membrane separates the object from the matching transmission medium. The object has no direct contact with the matching transmission medium. Preferably, the membrane is acoustically and optically matched for illuminating the object and detecting the acoustic signals. Acoustic matching means that acoustic reflections at the membrane's surface are minimized. Optical matching means that the membrane is made of a material being optically transparent for the wavelengths of the illumination/energy deposition. Advantageously, the membrane is made of at least one of polyvinyl chloride plastisol (PVCP), polyethylene and latex. The membrane has a thickness below 5 mm, preferably below 1 mm, e.g., below 200 µm to minimize acoustic and optical losses.

Our design incorporates the acoustically and optically matched membrane and allows a separation of the imaged object from the matching transmission medium into which the detector device is embedded for optoacoustic detection. This allows practical imaging applications without direct contact with the matching transmission medium, e.g., water.

Preferably, the holding device comprises a frame shaped holding element arranged for carrying the membrane. The membrane can be fixed to the frame shaped holding element such that a bag (or pocket, non-rigid container) is formed accommodating the object to be imaged. The membrane with the accommodated object can be immersed into the matching transmission medium in the container such that an upper side of the object is exposed to the surrounding gas atmosphere, e.g., air. The frame shaped holding element can be shaped in different shapes, for example, a half circular tube so that the center of mass of the object or the central axis of the object lie in the center of a curved ultrasonic detection array, also shaped in a partial circular geometry. This arrangement can lower the object within the matching transmission medium versus placing it on top of the matching transmission medium, thus allowing a better coverage of the acoustic responses generated from within the object by the corresponding surrounding multi-element detector. As a further advantage, the frame shaped holding element can be movable. To conduct the scanning movement, the frame shaped holding element can be moved along a guide rail in the container.

As a further advantage, utilizing the membrane allows imaging of living objects, e.g., animals. Accordingly, the imaging device can be provided with an anaesthesia device arranged for subjecting the object to an anaesthesia treatment.

The imaging device is adapted to conduct imaging and image reconstructing methods. To this end, the illumination device is adapted for illuminating the object with different wavelengths. Preferably, the illumination device comprises laser source with wavelength tuning Particularly preferred is a tunable optical parametric oscillator (OPO) laser including a tiltable non-linear crystal for wavelength scanning. It has been found, that this OPO device allows rapid wavelength changes adapted for the real time imaging.

In summary, this disclosure provides an efficient method and system in particular for non-contact multispectral optoacoustic tomography of whole body or localized regions of small animals in real time. To this end, the imaging device (signal collecting device) comprises the illumination device including an electromagnetic energy source, e.g., pulse laser source, and an acoustic signal detector device with a detector array and/or a single detector, including at least one acoustic detection element. Other sources include sources with frequencies in the kHz to GHz range, i.e., radiofrequencies and frequencies around them as discussed below. Preferably, the acoustically-matched membrane is provided separating the imaged object from a liquid medium where the at least one acoustic detection element is located. Advantageously, the membrane allows for the object to be imaged without being immersed into the liquid medium. According to the examples described below, the object is placed on top of a transparent membrane and illuminated with a laser source. The membrane is preferably made of optically transparent material that also does not significantly alter propagation of sound, e.g., acoustically-matched membrane. In this way, an efficient transmission of both laser radiation and the induced optoacoustic response is facilitated. The membrane also ensures that the imaged object can be conveniently placed for imaging without direct contact with water.

According to further independent solutions, the above objectives are achieved with imaging devices and/or methods modified according to the following aspects. With the following modifications, some features described above are replaced by modified features.

The multi-element array can be replaced by a single focused or unfocused detector element that will be scanned in the vicinity or around the object to acquire spatially resolved or tomographic data. This typically would represent a non-real time example, and it might be useful to image a localized area of an animal, for instance containing a tumor. In that case, by linear scanning of a spherically focused detector element along one or two dimensions using translation stage/s, 2D or 3D images of the region of interest can be obtained by using, e.g., delay-and-sum algorithm known from ultrasonic imaging. Illumination of the object is adjusted accordingly so that the light energy concentrates only in the region of interest. Using the single detector element is preferably combined with accommodating the object in the membrane.

The movement of the holding device relative to the optical components and the detector device can be replaced by a movement of the optical components and the detector device relative to the holding device, or combined movements of the optical components and the detector device and the holding device relative to each other.

The imaging with an optical generation of acoustic waves can be replaced by thermoacoustics imaging. In this case, the laser source of the illumination device is replaced by a generator device including an electromagnetic pulse source with frequencies, e.g., in the radiofrequency range. Furthermore the optical components would be replaced by irradiation components, like antennas or wave guides, which can be arranged outside the tank or in a sealed manner in the tank of the container device.

Our devices and methods are described in the following with exemplary reference to the structure and operation of the imaging device. Further details of the imaging and image reconstructing methods are implemented as described in PCT/EP2008/006142 and PCT/EP2009/004687. These applications are introduced into the present specification by reference, in particular with regard to the quantitative three-dimensional sensing and imaging of target tissue biomarkers and analyzing the acoustic signals, in particular in clinical, small animal and small organism imaging applications using multiple-wavelength illumination. The introduction of endogenous or exogenous reporter agents with molecular specificity, such as fluorescent proteins and probes, further allows the propagation of this technique towards molecular imaging applications. In this case, a promising approach is the use of multi-spectral illumination to differentiate specific spectral signatures of key reporter agents over the background tissue absorption. Combined, imaging of physiological and molecular markers using optoacoustics has the potential to high resolution photonic imaging, through depths that go significantly beyond the capabilities of modern microscopy.

FIG. 1 illustrates a preferred example of the imaging device 100 including an illumination device 10, a detector device 20, a control device 30, and a container device 50 comprising a tank 51. The control device 30 is arranged to control the illumination device 10 and the detector device 20 and to conduct the steps of the image reconstructing methods. The tank 51 contains a matching transmission medium 53, e.g., water or oil. The illumination device 10 comprises a laser source 11 and optical components 17, 18, e.g., optical fibers or mirrors arranged in the water tank 51. The container device 50 further includes a holding device comprising a transparent membrane 55. The object 1, e.g., a mouse has a main extension (longitudinal direction, object axis) representing, e.g., the z-direction.

According to FIG. 1, the object 1 illuminated with the laser source 11 is placed on top of the transparent membrane 55. The membrane 55 is made of optically transparent material that also does not significantly alter propagation of sound, e.g., acoustically-matched membrane made of polyvinyl chloride plastisol (PVCP) or thin films of polyethylene. In this way, an efficient transmission of both laser radiation and the induced optoacoustic response is facilitated. The membrane 55 also ensures that the imaged object 1 can be conveniently placed for imaging without direct contact with water. The membrane 55 is placed in contact with the water tank 51, into which the detector array 21 is immersed.

The detector array 21 is, e.g., a curved array with 64 acoustic detection elements 22, which form, for example, a 180° arc that surrounds the object 1. In the example of FIG. 1, all the acoustic detection elements 22 are cylindrically focused in the detection plane to allow for simultaneous collection of signals from a two-dimensional detection plane (drawing plane, x-y-plane). The imaging device 100 will therefore collect two-dimensional data in real time.

Figure 2:
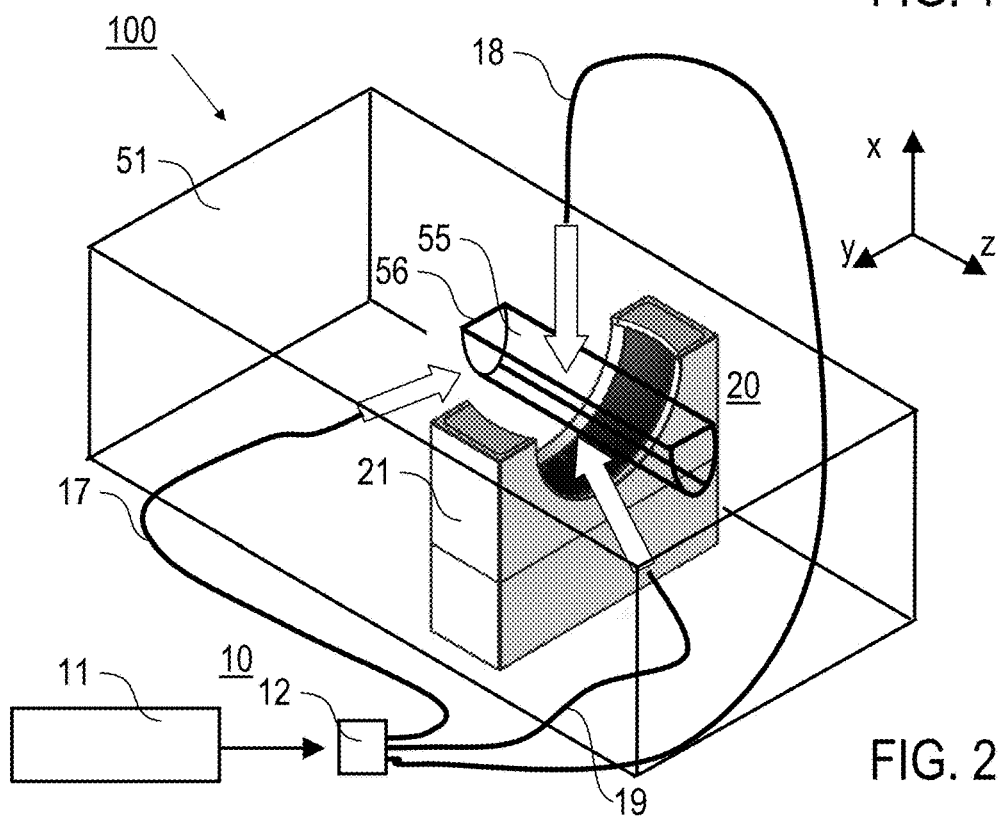

A schematic perspective view of the imaging device 100 according to a modified example is presented in FIG. 2. The illumination device 10 comprises a laser 11 and optical components 17, 18 and 19 fixedly arranged in the container 51 for illuminating the object 1 (not shown) in the bag-shaped membrane 55. The optical components 17, 18 and 19 comprise optical fibers into which light pulses emitted by the laser 11 are coupled using an optical coupler 12. The detector device 20 comprises an array 21 of detector elements integrated in a common block. The detector device 20 is fixedly positioned on the bottom of the container 51. Both the illumination device 10 and the detector device 20 are connected with a control device (not shown).

As an alternative, plane or curved mirrors could be used as optical components 17, 18 and 19 for illuminating the object from different sides. Light from a laser source could be coupled to the mirrors through an upper surface of the matching transmission medium 53 in the tank 51, so that distortions by the tank walls are suppressed.

A holding device 55, 56 is arranged for positioning and moving the object relative to the optical components 17, 18 and 19 of the illumination device 10 and relative to the detector device 20. The movement is directed perpendicular to the detection plane, i.e., in z-direction. The holding device comprises the membrane 55 and a frame shaped holding element 56 to which the membrane 55 is attached. The frame shaped holding element 56 is supported by guide rail in the container device as further illustrated in FIG. 3. The membrane 55 can provide a bag supporting the object from below as shown in FIG. 1 or an envelope covering the object from multiple sides. In particular, the membrane may have a tube or hose shape. In this case, the complete membrane can be immersed into the matching transmission medium, while the ends thereof are closed or located above a surface of the matching transmission medium.

Figure 3:
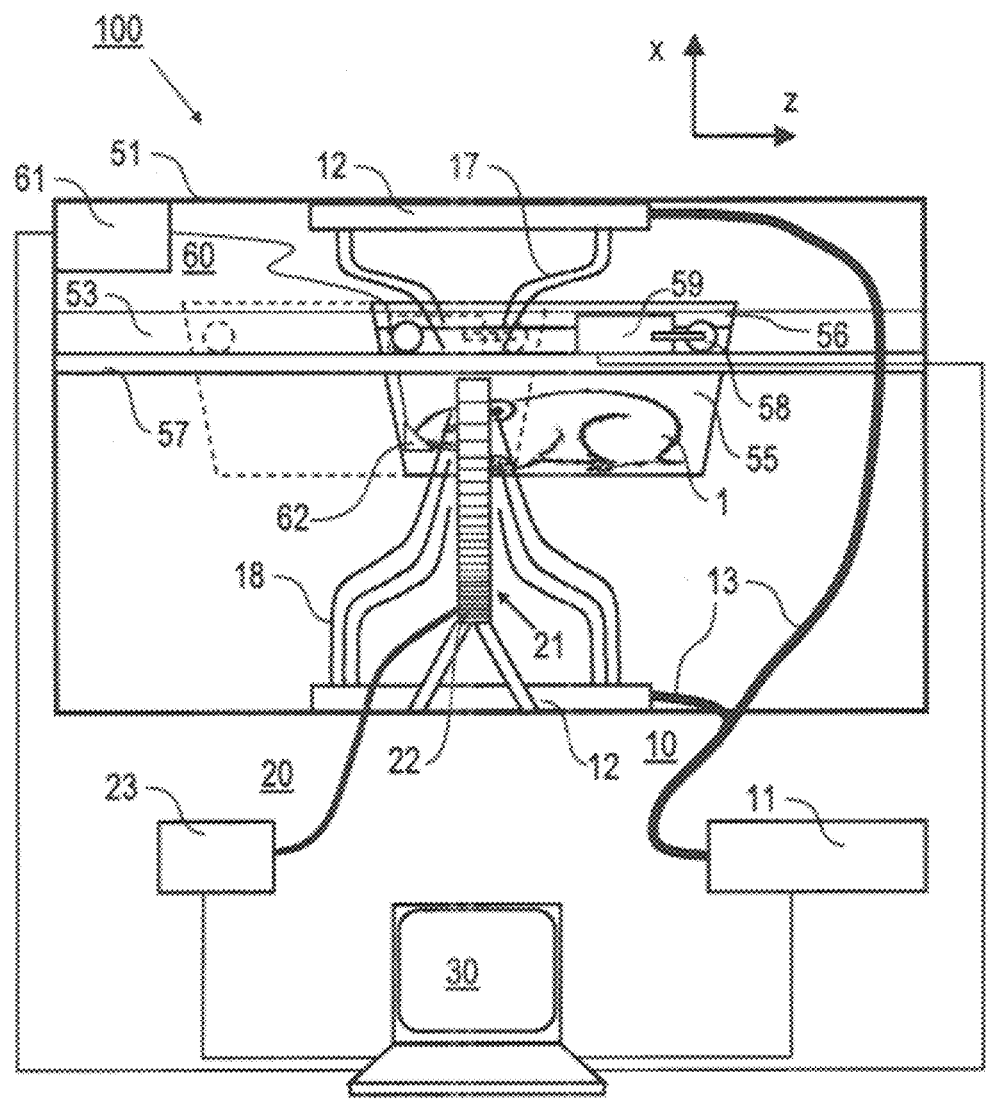
FIG. 3 is a schematic illustration of further details of a first example of the imaging device.

A schematic side view of the imaging device 100 according to a further modified second example is presented in FIG. 3. The illumination device 10 comprises a laser 11 being connected via light-guiding fibres 13 to optical couplers 12. The optical couplers 12 are connected with a plurality of fixedly arranged optical fibers 17, 18 the output ends of which facing to the object 1. The optical fibers 17, 18 are schematically illustrated with mutual distances. In practice, the optical fibers 17, 18 are arranged such the output ends thereof are located on a circle line surrounding the bag-shaped membrane 55 and the object 1.

To attain optimal quality of tomographic reconstructions, the light is shined upon the imaged object from multiple directions to ensure uniform illumination of the object at the imaging plane. This can be done by, e.g., guiding the light by means of splitting a free-space beam or, as illustrated, using a fiber bundle. Preferably, the bundle splits into 10 arms that are placed in the vicinity of the imaged object and illuminate it from 10 equally-spaced angles adding up to 360°. Optimally, the illuminating light forms a ring-type pattern on the object's surface. The effective width of this illumination ring is optimally adjusted to achieve maximal possible confinement of excitation light intensity within the imaged plane (cross-section) of the object. This can be done by, for instance, minimizing the light width to a minimal permissible value so that the safety limits of tissue exposure to pulsed laser radiation are met, e.g., the fluence on the tissue surface does not exceed 20 $mJ/cm^2$ at a wavelength of 750 nm as proposed in "American National Standards for the Safe Use of Lasers," ANSI Z136.1, American Laser Institute, 2000.

The detector device 20 comprises an array 21 of detector elements 22 being connected with a signal recorder 23 outside the container 51. The illumination device 10 and the detector device 20 are connected with the control device 30. The detector elements 22 are selected in view of the requirements for high resolution and quality optoacoustic tomographic reconstructions that directly correspond to the detection bandwidth, which should ideally be as large as possible. For this one could use ultrawideband ultrasound detection technologies, detectors including piezoelectric polymers such as pVDF film detectors and Fabry-Perot interferometric detector elements that have already proven to be a potential tool for high-resolution optoacoustic imaging in vivo. Compared to the latter broadband approaches, PZT and other piezocomposite technologies can normally provide higher SNR and robustness, in exchange however for narrower bandwidth.

Figure 4:
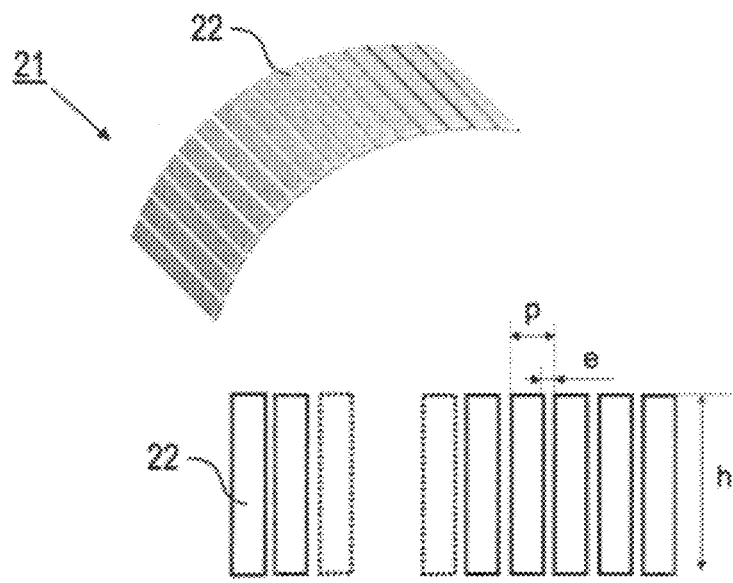
FIG. 4 shows details of an array of detector elements used in the imaging device.

Preferably, the detector array 21 is a curved concave array with acoustic detector elements 22 as shown in FIG. 4. As an example, the number of acoustic detector elements 22 is selected in the range of 64 to 256. The detector elements 22 form, for example, a 180° arc that surrounds the object 1. In the example of FIG. 4, each one of the strip-shaped acoustic detection elements (Pitch p=0.98 mm; Height h=15 mm; Inter element spacing e=0.1 mm) is cylindrically or spherically focused in the detection plane to allow for simultaneous collection of signals from a two-dimensional detection (imaging) plane in real time. For example, given pulsed laser source with 10 Hz repetition frequency, in plane 2D data can be collected every 100 ms per single wavelength. The magnitude of the recorded optoacoustic signals is normally directly proportional to the detector's area while the noise floor decreases only as a function of square root of the number of averages or measurements. As a result, a single focused element 22 will, for instance, be way more superior in terms of SNR to multi-element array spread over the same detection area. The acoustic focusing if thus used here to increase detection area and sensitivity, in exchange for compromising image quality and resolution along dimensions where focusing is performed. This solution comprises therefore a sort of compromise between acquisition speed and imaging performance.

A guide rail 57 is located in the container 51 for carrying the frame shaped holding element 56 as shown in FIG. 3. The frame shaped holding element 56 is provided with wheels 58 running on the guide rail 57 and an electric motor 59 connected with the control device 30. The membrane 55 with the object 1 is moved in z-direction by actuating the electric motor 59. As an example, the object can be scanned from the illustrated position to the position shown with dashed lines. For implementing a movement of the optical components and the detector device relative to the holding device, a guide rail and a drive unit can be arranged in the container, e.g., on a bottom surface thereof.

FIG. 3 further illustrates an anesthesia device 60 which comprises an anesthesia gas source 61 and a mask 62 to be set on the head of a living object under investigation, like a mouse. The anesthesia device 60 is structured as it is known from animal holders used, e.g., for X-Ray CT or MRI investigations.

To conduct the imaging method, the object 1 is positioned on the membrane 55 in the container 51. As an example, a nude (hairless) mouse subjected to an anesthesia is set on the membrane 55. The membrane is placed in contact with the matching transmission medium 53 into which the ultrasonic detection array 21 is immersed.

Subsequently, a three-dimensional data acquisition is achieved via scanning the imaged object 1 across the illumination-detection plane that remains stationary or vice versa. Image reconstruction can be achieved, e.g., by using cylindrical or spherical Radon-based back-projection algorithm. Preferably, in the multispectral imaging applications, the laser wavelength is scanned at each imaging plane so that the full set of tomographic data is collected at all the required wavelengths prior to moving the object or imaging plane to another location. This is done since some biomarkers may present only small variations of the optical absorption over highly absorbing background, in which case even small quantification inaccuracies may lead to uninterpretable results.

Figure 5:
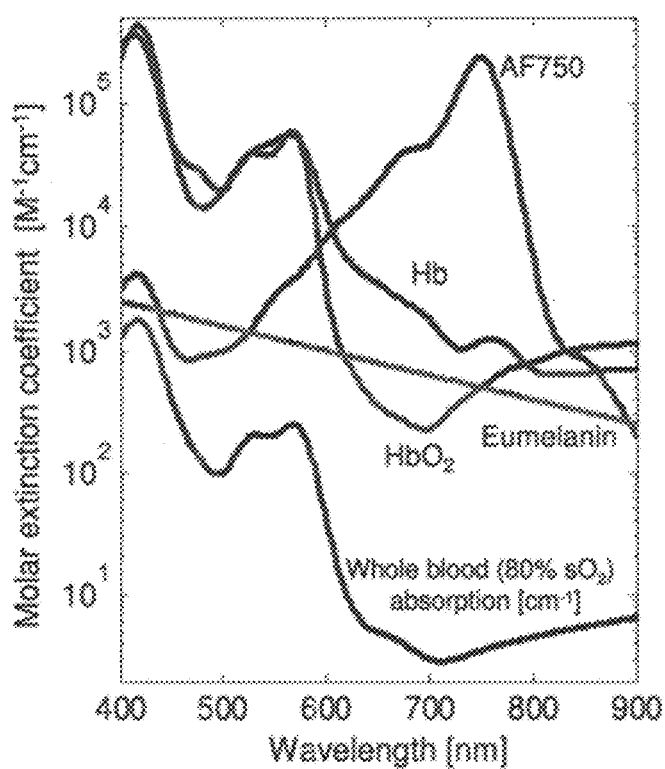
FIG. 5 is a graphical representation of a wavelength dependence of molar extinction of AF750 and common tissue chromophores.

Preferably, fast wavelength scanning is performed by the tunable optical parametric oscillator (OPO) laser. For instance, to attain highly sensitive detection of AlexaFluor750™ (AF750) molecular probe in tissue, whose characteristic spectrum is shown in FIG. 5, one could perform optoacoustic imaging with several wavelengths around the peak extinction of the probe, e.g., with 5 wavelengths (710, 730, 750, 770, 790 nm). With pulse repetition rate of 10 Hz, i.e., each pulse is fired every 100 ms, the output wavelength of the OPO laser will be repetitively scanned in the range 710-790 nm (with the speed of 20 nm per 100 ms) by continuously shifting the angle of the BBO ($BaB_2O_4$) nonlinear crystal with the respect to the pumping beam direction inside the OPO. In this case, a full set of multispectral tomographic data is acquired every 500 msec. The approach therefore ensures robust and reproducible results since the full set of multispectral data is acquired while the object remains fully stationary with respect to both illuminating light source/s and detector/s.

Figure 6:
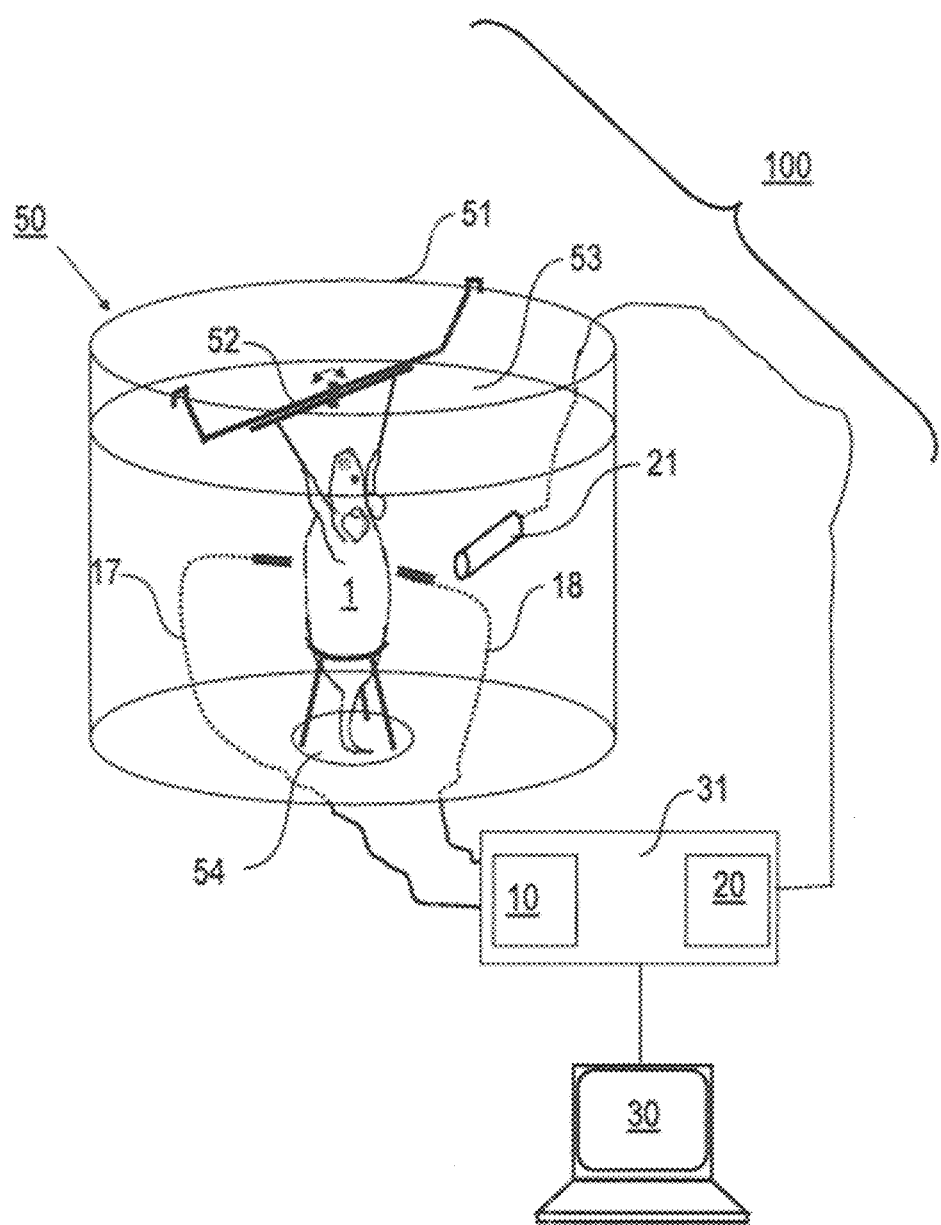
FIG. 6 is a schematic illustration of another example of the imaging device.

FIG. 6 illustrates another imaging device 100 for biomedical imaging of mesoscopic-size objects and small animals, like mice or other rodents, flies, fishes, worms, animal embryos. The imaging device 100 comprises the illumination device 10, the detector device 20 and the control device 30. Furthermore, the container device 50 is provided, which comprises the tank 51 and holding elements 52, 54 which are adapted for positioning components of the imaging device 100. The tank 51 contains the matching transmission medium 53, e.g., water or oil. The object to be investigated (living mouse 1) is positioned on the lower part 54 of the rod or plate shaped holding element.

Preferably, the illumination light comprises at least one characteristic wavelength of at least 100 nm, preferably at least 400 nm, particularly preferred at least 650 nm, and below 5000 nm, preferably below 1200 nm, particularly preferred below 850 nm. For this example, the illumination device 10 includes a laser source device being adapted for emitting light pulses, preferably in the visible or near-infrared spectra. The light pulses preferably have a duration below 1 µs, particularly preferred below 50 ns.

The illumination device 10 and the detector device 20 are partially integrated in a casing 31, that is arranged outside the container device 50. The illumination device 10 comprises a pulsed laser source whose light is directed to the mouse 1 from two opposite directions 17,18 by, e.g., using optical mirrors or fibers. The detector device 20 comprises an array 21 of acoustic detector elements. The detector device 20 is arranged in the neighbourhood of the holding element 52 with the mouse 1. Advantageously, there are no particular restrictions with regard to the position of the detector device 20. The preferred location, however, will be as close as possible to the object to obtain measurements with high signal-to-noise ratios. To implement the above image reconstruction, it is only necessary to have information on the location of the array of detector elements relative to the object (mouse 1).

The examples schematically illustrated in the figures are not restricted to the investigation of small animals. Alternatively, other biological objects can be imaged, e.g., human beings or larger animals or parts thereof. As an example, tank 51 can be adapted for accommodating a part of a human patient instead of the mouse 1.

While our devices and methods described above with reference to the use of an array of detector elements for implementing using a single detector element, the array is to be replaced by a combination of the single detector element and at least one translation stage.

The invention claimed is:

1. An imaging device configured for optoacoustic imaging of an object, comprising:
    an illumination device comprising optical components and a laser source, the laser source being configured to illuminate the object via the optical components from different directions, so that an illumination pattern is formed upon the object, the optical components comprising optical fibers;
    a detector device comprising an array of detector elements configured to detect acoustic signals created in the object in response to illuminating the object, wherein the shape of the array of detector elements is an arc having a center of curvature, the center of curvature lying within the object during imaging of the object, and wherein the detector elements are disposed such that they are focused into a predetermined 2D detection plane through which the object is imaged upon use of the imaging device;
    a container device accommodating the optical components, the detector device, and a matching transmission medium;
    a motor; and
    a membrane and a frame-shaped holding element to which the membrane is attached, the membrane forming a bag configured to support the object from below and configured to immerse the object in the matching transmission medium, whereby the membrane separates the object and the matching transmission medium from each other such that the object has no direct contact with the matching transmission medium, the frame-shaped holding element being supported by a guide rail located in the container device, the frame-shaped holding element including a plurality of wheels configured to run on the guide rail, the motor configured to move the frame-shaped holding element relative to the container device, the illumination device, and the detector device along a path of translation movement, the path of translation movement being perpendicular to the predetermined 2D detection plane, wherein output ends of the optical fibers are facing to the object and surrounding the membrane and the object, and wherein the arc-shaped array of detector elements partially surrounds the object and the membrane while the membrane with the object is moved relative to the illumination device and the array of detector elements along the path of translation movement.

2. The imaging device according to claim 1, wherein the detector elements comprise at least one of piezoelectric film detector elements and film detector elements adapted for interferometric signal recording.

3. The imaging device according to claim 1, wherein the illumination pattern formed upon the object is a ring type pattern.

4. The imaging device according to claim 1, wherein the optical fibers comprise a fiber bundle having multiple arms arranged at equally spaced angles adding up to 360 degrees.

5. The imaging device according to claim 1, wherein the membrane is acoustically and optically matched to illuminate the object and detect the acoustic signals.

6. The imaging device according to claim 1, wherein the laser source comprises a tunable optical parameter oscillator laser including a tiltable non-linear crystal for wavelength scanning.

7. The imaging device according to claim 1, wherein the membrane is made of at least one of polyvinyl chloride plastisol, polyethylene, or latex.

8. The imaging device according to claim 1, wherein the membrane has a thickness below 1 mm.

9. The imaging device according to claim 1, wherein the illumination device and the detector device are configured to repeat illuminating the object and detecting acoustic signals for at least two different wavelengths in less than 2 seconds.

10. The imaging device according to claim 1, wherein the membrane forming the bag is a tube-shaped membrane, such that when the tube-shaped membrane is immersed in the matching transmission medium, ends of the tube-shaped membrane are located above the surface of the matching transmission medium.

11. The imaging device according to claim 1, further comprising a control device configured to actuate the motor to move the membrane with the object along the path of translation movement to stepwise adjust positions of the object relative to the 2D detection plane, to control the illumination device to repeatedly illuminate the object at each of the adjusted positions with at least two different wavelengths of illumination light, and to control the detector device to repeatedly detect acoustic signals created in the object at each of the adjusted positions in response to the repeated illuminating of the object with the at least two different wavelengths of the illumination light, and to reconstruct images of the object by analyzing the acoustic signals created in the object at each of the adjusted positions of the object in response to the repeated illuminating with the at least two different wavelengths, whereby a series of slice images of the object is obtained for each of the at least two different wavelengths.

12. The imaging device according to claim 1, wherein the output ends of the optical fibers are located on a circle line surrounding the membrane and the object.

13. An imaging device for optoacoustic imaging of an object, the imaging device comprising:
   an illumination device comprising optical components and a laser source, the laser source configured to illuminate the object via the optical components from different directions such that an illumination pattern is formed on the object, the optical components comprising optical fibers;
   a detector device comprising an array of detector elements configured to detect acoustic signals created in the object in response to illuminating the object, wherein the shape of the array of detector elements is an arc having a center of curvature, the center of curvature lying within the object during imaging of the object, wherein the detector elements of the array of detector elements are disposed such that they are focused into a predetermined 2D detection plane through which the object is imaged upon use of the imaging device;
   a container device accommodating the optical components and the detector device;
   a matching transmission medium disposed in the container device;
   a frame-shaped element attached to a membrane, the membrane forming a bag to support the object from below, wherein the membrane is configured to immerse the object in the matching transmission medium, and wherein the membrane is further configured to separate the object and the matching transmission medium such that the object has no direct contact with the matching transmission medium;
   a guide rail disposed in the container device, the guide rail supporting the frame-shaped element, the frame-shaped element including a plurality of wheels configured to run on the guide rail; and
   a motor operatively coupled to the frame-shaped element, wherein upon actuation of the motor the motor is configured to move the frame-shaped element along the guide rail such that the membrane and the object move relative to the container device, the illumination device, and the array of detector elements along a path of translation movement, wherein the path of translation movement is perpendicular to the predetermined 2D detection plane, and wherein output ends of the optical fibers are facing to the object and surrounding the membrane and the object, and wherein the array of detector elements partially surrounds the object and the membrane while the membrane with the object is moved relative to the illumination device and the detector device.

14. The imaging device according to claim 13, wherein the output ends of the optical fibers are located on a circle line surrounding the membrane and the object.

* * * * *

UNITED STATES PATENT AND TRADEMARK OFFICE
CERTIFICATE OF CORRECTION

PATENT NO. : 10,292,593 B2
APPLICATION NO. : 13/386491
DATED : May 21, 2019
INVENTOR(S) : Razansky et al.

It is certified that error appears in the above-identified patent and that said Letters Patent is hereby corrected as shown below:

In the Specification

Column 2, Line 57 reads, ". . . therefore be helpful is to provide . . ." which should read, ". . . therefore be helpful to provide . . ."

Column 4, Line 40 reads, "multiple position, . . ." which should read, "multiple positions . . ."

Column 4, Line 66 reads, ". . . to the objects axis . . ." which should read, ". . . to the object's axis . . ."

Column 6, Line 55 reads, ". . . with wavelength tuning Particularly . . ." which should read, ". . . with wavelength tuning. Particularly . . ."

Column 8, Line 5 reads, ". . . to high resolution . . ." which should read, ". . . to provide high resolution . . ."

Column 9, Line 14 reads, ". . . light-guiding fibres . . ." which should read, ". . . light-guiding fibers . . ."

Column 9, Line 19 reads, ". . . are arranged such . . ." which should read, ". . . are arranged such that . . ."

Signed and Sealed this
Fifth Day of November, 2019

Andrei Iancu
*Director of the United States Patent and Trademark Office*